US011442129B1

(12) United States Patent
Fournier et al.

(10) Patent No.: US 11,442,129 B1
(45) Date of Patent: Sep. 13, 2022

(54) SYSTEMIC CERTAINTY OF EVENT CONVERGENCE

(71) Applicant: DeCurtis, LLC, Orlando, FL (US)

(72) Inventors: Derek Fournier, Valrico, FL (US); James Learish, Cary, NC (US); Paul Schottland, Fort Mills, SC (US); Matthew Winans, Virginia Beach, VA (US)

(73) Assignee: DeCurtis, LLC, Orlando, FL (US)

( * ) Notice: Subject to any disclaimer, the term of this patent is extended or adjusted under 35 U.S.C. 154(b) by 0 days.

(21) Appl. No.: 17/229,236

(22) Filed: Apr. 13, 2021

(51) Int. Cl.
| | | |
|---|---|---|
| G01S 1/04 | (2006.01) |
| H04W 4/80 | (2018.01) |
| H04W 4/029 | (2018.01) |
| A61B 5/00 | (2006.01) |
| G06T 7/70 | (2017.01) |
| G08B 21/24 | (2006.01) |

(52) U.S. Cl.
CPC ............ *G01S 1/0423* (2019.08); *A61B 5/002* (2013.01); *A61B 5/0013* (2013.01); *G01S 1/0428* (2019.08); *G06T 7/70* (2017.01); *G08B 21/24* (2013.01); *H04W 4/029* (2018.02); *H04W 4/80* (2018.02); *G06T 2207/10048* (2013.01); *G06T 2207/30196* (2013.01)

(58) Field of Classification Search
CPC ..... G01S 1/0423; G01S 1/0428; A61B 5/002; A61B 5/0013; H04W 4/80; H04W 4/029; G08B 21/24; G06T 7/70; G06T 2207/10048; G06T 2207/30196
See application file for complete search history.

(56) References Cited

U.S. PATENT DOCUMENTS

| | | | |
|---|---|---|---|
| 8,849,205 B2 | 9/2014 | Desai et al. |
| 8,862,067 B2 | 10/2014 | Un et al. |
| 9,357,342 B2 | 5/2016 | Viswanadham et al. |
| 9,418,531 B2 | 8/2016 | Basalamah et al. |
| 9,485,603 B2 | 11/2016 | Worrall et al. |
| 9,774,985 B2 | 9/2017 | Weizman et al. |
| 9,875,588 B2 | 1/2018 | Mccollum et al. |
| 10,037,642 B2 | 7/2018 | Padgett et al. |
| 10,045,184 B2 | 8/2018 | Padgett et al. |
| 10,049,516 B2 | 8/2018 | Padgett et al. |
| 10,140,649 B2 | 11/2018 | Drake et al. |
| 10,157,514 B2 | 12/2018 | Padgett et al. |
| 10,171,978 B2 | 1/2019 | Padgett et al. |
| 10,238,976 B2 | 3/2019 | Ackley et al. |
| 10,304,271 B2 | 5/2019 | Padgett et al. |

(Continued)

FOREIGN PATENT DOCUMENTS

EP    3046342 A1    7/2016

*Primary Examiner* — James J Yang

(57) ABSTRACT

Systems, methods, and computer-executable instructions for identifying a convergence of objects includes receiving, at a device, a first beacon from a beacon transmitter located within a first location. A first location is identified based on the first beacon. A second beacon is received that is transmitted from a wearable worn by a patient. The patient associated with the second beacon is identified. A convergence time and a previous convergence time of the patient and device are determined. An out of compliance event based on the current convergence time and the previous convergence time is determined. An alert is generated based on the out of compliance event. The alert includes the first location.

20 Claims, 4 Drawing Sheets

(56) References Cited

U.S. PATENT DOCUMENTS

| | | |
|---|---|---|
| 10,499,228 B2 | 12/2019 | Padgett et al. |
| 2007/0132597 A1* | 6/2007 | Rodgers ................. G06Q 10/10 348/E7.078 |
| 2013/0218583 A1* | 8/2013 | Marcolongo .......... G16H 15/00 705/2 |
| 2013/0267791 A1* | 10/2013 | Halperin .............. A61B 5/6892 600/300 |
| 2014/0122148 A1 | 5/2014 | Padgett et al. |
| 2016/0183042 A1 | 6/2016 | Weizman et al. |
| 2016/0217496 A1 | 7/2016 | Tuchman et al. |
| 2016/0373893 A1 | 12/2016 | Khanna et al. |
| 2017/0186301 A1* | 6/2017 | Vaddepally .......... G08B 21/245 |
| 2018/0276434 A1 | 1/2018 | Li et al. |
| 2018/0052655 A1* | 2/2018 | Hannibal, III ......... H04R 29/00 |
| 2020/0059774 A1 | 2/2020 | Padgett et al. |

\* cited by examiner

SYSTEMIC CERTAINTY OF EVENT CONVERGENCE

BACKGROUND

Patient safety checks are done at various facilities to ensure patients are safe and receive proper care. One example of a patient safety check is a Q15 safety check, standing for a safety check that is done every 15 minutes. Safety checks may also be done at various different intervals, such as every 30 minutes, 60 minutes, etc. Current procedures have staff visibly watch a patient and then document observations of the patient via a written form. Observations may require a staff member to be within so many feet of a patient, confirm signs of life, patient location, etc. Observation forms may be stored for a long time. Audits regarding compliance to a safety check protocol are proven via these written forms. Compliance with safe check protocols, however, can only measure historical compliance. New systems that can ensure near real-time compliance or lack thereof of safety protocols are needed.

DETAILED DESCRIPTION

Ensuring compliance with patient safety protocols, such as Q15 protocols, results in patients receiving excellent care. These protocols are designed for the protection of patients. Accordingly, facilities that are not in compliance with safety protocols risk increased institutional risk; unhappy patients and employees; reduced quality of care; and potential loss of time and money. Various disclosed embodiments herein describe systems that help ensure compliance and identify out of compliance activity in an unobtrusive and time sensitive manner. Other protocols that use a schedule to check performance of a task may also benefit from the disclosed embodiments. For example, minors that travel alone have mandatory touch bases whose compliance can be monitored with disclosed embodiments. In addition, procedures for monitoring equipment or locations may benefit from the disclosed embodiments.

Figure 1:
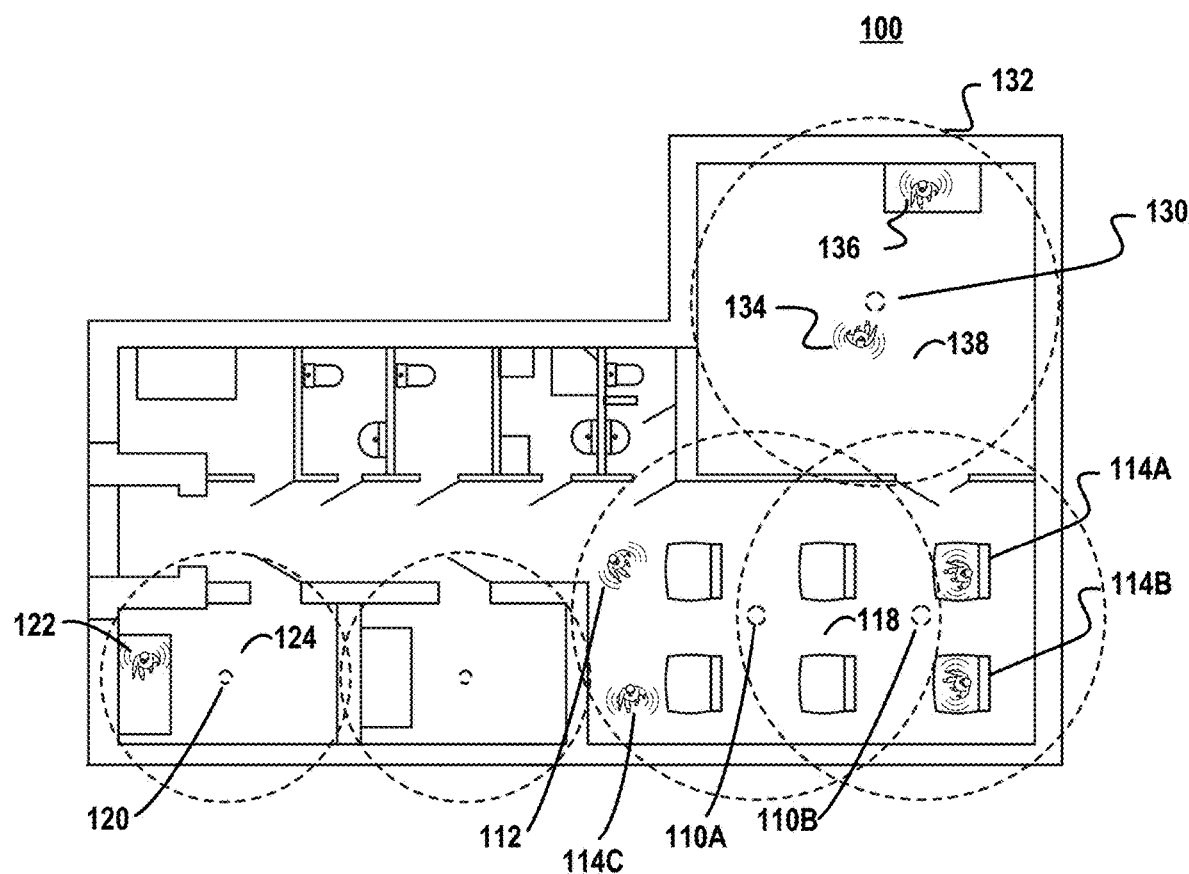
FIG. 1 is a system diagram of a system for showing systemic certainty of event convergence in accordance with respective examples.

FIG. 1 is a system diagram of a system 100 for showing systemic certainty of event convergence in accordance with respective examples. The illustrated system 100 may be for an office building such as a doctor's office. Within the office, a number of beacon transmitters 110A, 110B, 120, and 130 are installed at fixed locations within the office. The beacon transmitters transmit a beacon that includes an identifier. The identifier is mapped to the location where the beacon transmitter is installed. Accordingly, the beacon transmitter 120 transmits a beacon that identifies a room 124. Another beacon 130 transmits a beacon that identifies a room 138. The range of beacon transmitters may be configured based on the location where a beacon transmitter is installed. For example, range 132 of the beacon transmitter 130 may be large enough to encompass the majority or relevant portions of the room 138. Other beacon transmitters, such as the beacon transmitter 120, may have smaller ranges to take into account the size of the room 124 where the beacon transmitter 120 is installed.

Multiple beacon transmitters may be used in conjunction to identify a larger area. For example, beacon transmitters 110A and 110B combined cover a waiting room 118. In one example, the beacon transmitters 110A and 110B may transmit the same identifier that identifies the waiting room 118. In another example, the beacon transmitters 110A and 110B transmit different identifiers, each of which is associated with the waiting room 118.

Individuals and objects may move around the office. In an example, patients may be provided with a wearable that includes a beacon transmitter. The wearable may be a bracelet, a fob, a card, etc. The wearable transmits a beacon that includes an identifier that identifies a patient. Accordingly, patients 114A, 114B, and 114C each have a wearable. These wearables transmit a beacon with a unique identifier. The unique identifier is used to identify patient 114A from other patients, staff, objects, etc.

Staff may use a device that includes an application that receives beacons from both beacon transmitters and wearables. For example, a staff member 112 may carry a tablet with the application running. The application may receive beacons from the patients 114A, 114B, and 114C as the staff member walks around the waiting room 118. In addition, the application on the device may receive the beacons from the beacon transmitters 110A and 110B. With the various received beacons, convergence between the staff member 112 and the patients 114A, 114B, and 114C within the waiting room can be determined.

In one example, the application asks the staff member which patients are being observed. The application may determine from received beacons which patients are nearby. Patient information, such as name, previous location, picture, etc., may be accessed by the device. For example, the device may query a remote database for this information. Alternatively, the device may have some or all of this information stored locally. The application may display this information for the staff member 112 to select which patients are being observed. A log of the observation for each observed patient may be stored on the device. The device may also transmit the log to a remote server that collects observation logs from multiple devices.

In one example, staff log into the application by providing credentials as known in the art. Once logged in, the application associates all logs generated with by the application with the logged in staff member. For example, the staff member's login id or other identifier is provided within an observation log. In another example, a staff member also wears a wearable that transmits an identifier associated with the staff In this example, the device receives the beacon associated with the staff along with the location beacon and patient beacon. The device identifies the staff for observation logs based on the beacon associated with the staff. For example, the device may determine a received beacon identifier is associated with a staff member. The staff member's identifier may then be provided within the observation logs. In an example, the device may receive multiple beacons associated with staff members. In an example, the beacon with the strongest received power from the multiple beacons is determined to be the staff member using the device. In addition, the device may keep a history of received staff beacons. The staff beacon that has remained constant for more than a predetermined amount of time, e.g., 1 minute, 5 minutes, etc., is determined to be the staff using the device. This example accounts for staff members that pass one another in the office or stop and talk. As another example, the staff beacon combined with the login information is used to verify which staff member is observing patients. This example, also provides a way to check if another staff member or another individual has picked up the device. In this example, the device may provide an indication that the user of the device is not the logged in staff member. The device may automatically log out the staff member and ask for new credentials.

In an example, a staff member 134 uses a device. The device identifies the staff member 134 via login credentials, staff member beacon identifier, or a combination of both. An application on the device may provide the staff member 134 with a list of patients that need to be observed. For example, the application may indicate that patient 136 located in room 138 needs to be visited. As the staff member enters the room 138 and comes within proximity of the patient wearable, the device receives the patient beacon associated with the patient 136. In one example, the distance between the device and the patient 136 is determined. For example, using the received signal strength of the patient beacon at the device may be used to estimate the distance between the device and the patient. An application may restrict the ability to generate an observation log until the device comes within a predetermined distance of the patient 136. In addition, an average distance and time the device was within the vicinity of the patient may be determined and included as part of an observation log.

The device also receives a location beacon from the beacon transmitter 130. The device or application running on the device, may then determine that the staff member 134 has converged with the patient 136 in the room 130. An observation log may then be created indicating the staff member 134, the room 130, and the patient 136. The application may also ask for information from the staff member 134 regarding the patient 136. For example, how the patient 136 looks, behavior of the patient 136, etc., This information may be included in the observation.

In addition, the room 130 may include monitoring equipment (not shown) that monitors the patient 136. For example, a heart rate and oxygen level monitor may monitor the patient 136. In an example, the equipment may also include an associated beacon transmitter that transmits an identifier associated with the equipment. This identifier of equipment may be received by the device and included within the observation log. Observation logs may also include a timestamp. In one example, a remote device that receives the observation log may query the equipment or data store of data from the equipment to determine the data at the relevant time for the patient. For example, the remote device may use the equipment identifier to identify which equipment to query and the timestamp to determine the relevant time. In another example, the device may receive this information directly from the equipment or queries the equipment for the information. This equipment data may then be incorporated into the observation log sent to the remote device.

A patient 122 may be waiting in a room 124. When the patient 122 was led to the room 124, a staff member's device logged the location of the patient 122 being in room 124. For example, the staff member's device would have received the patient's beacon as well as the location beacon associated with room 124 from the beacon transmitter 124. If the remote sever does not receive information regarding the location of the patient 122 for a period of time, an alert may be transmitted to staff. For example, if the facility is doing Q15 status checks, the remote server may indicate that after 10 minutes of not receiving observation log data associated with the patient 122, the remote server may alert staff that the patient 122 needs an observation within the next five minutes. The remote server may send alerts to all staff devices, to the staff assigned to the patient 122, or to staff that are located near room 124.

To determine compliance with a time based protocol, a remote server may log the initial interaction with a patient. For example, when a patient arrives at a facility and checks into the facility, a patient wearable is assigned to the patient. An entry system associates the identifier of the patient wearable with the patient. An entry timestamp may be logged as part of an initial observation log. The initial observation log may be entered manually to start a compliance timer associated with the patient. The initial observation may also indicate a location within the facility where the patient is assigned. For example, the patient may be assigned to a waiting room, such as the waiting room 118.

As the patient waits in the waiting room 118, the staff member 112 observes the patient and supplies an observation log of the patient to a remote server. The remote server may reset or restart the compliance timer associated with the patient. In an example, the patient may be the patient 122 that has been moved to the room 124 and is waiting to be seen. As the staff of the facility may be overworked or understaffed, the patient 122 may be waiting for 10 minutes without being observed. The remote server may keep a list of all patients within the facility, with each patient having an associated timer. The timers may be monitored by the remote server. As there may be different observation intervals, patient timers may be associated with a time interval, such as 15 minutes. The remote server may monitor the timers to determine if any timer is close to the interval or is about to expire. For example, for Q15 observations, timers that count up from the last observation issues an alert when the timer reaches 10 minutes. Other thresholds such as 12 minutes, 13 minutes, etc., may be used. These thresholds can also be used in combination with one another.

As an example, the patient 122 in the room 124 has an associated observation timer. When this observation timer reaches 10 minutes or if counting down reaches 5 minutes, an alert is generated. The alert may include an indication of the room 124 and the patient 122. The alert may be sent to all staff members of staff members associated with the patient 122.

If the patient 122 is not observed before the timer expires or reaches its compliance threshold, an alert may be created and sent to staff regarding an out of compliance event. This information may be logged. The remote server may also provide additional logging or alerting based on an out of compliance event. Eventually, the patient 122 is observed. Based on the timestamp associated with this observation, a total amount of time that the facility was out of compliance may be determined. From the information received by the remote server from various staff members, a compliance dashboard may be created. The dashboard may include how many out of compliance events there were, how much time the facility was in compliance, time spent out of compliance, etc.

As an additional safety feature, if the patient 122 leaves the room 124, the remote server may provide an alert. For example, the remote server may determine the patient 122 is to be within the room 124 through previous observation reports or directly from staff. Beacon readers may be installed in the facility or readers from staff devices may detect the patient beacon as the patient 122 wanders out of the room 124. The remote server may check the allowed areas for the patient 122 and determine that the patient 122 has entered into unallowed areas. Alerts may be generated for the staff indicating that the patient 122 has entered a restricted area.

Figure 2:
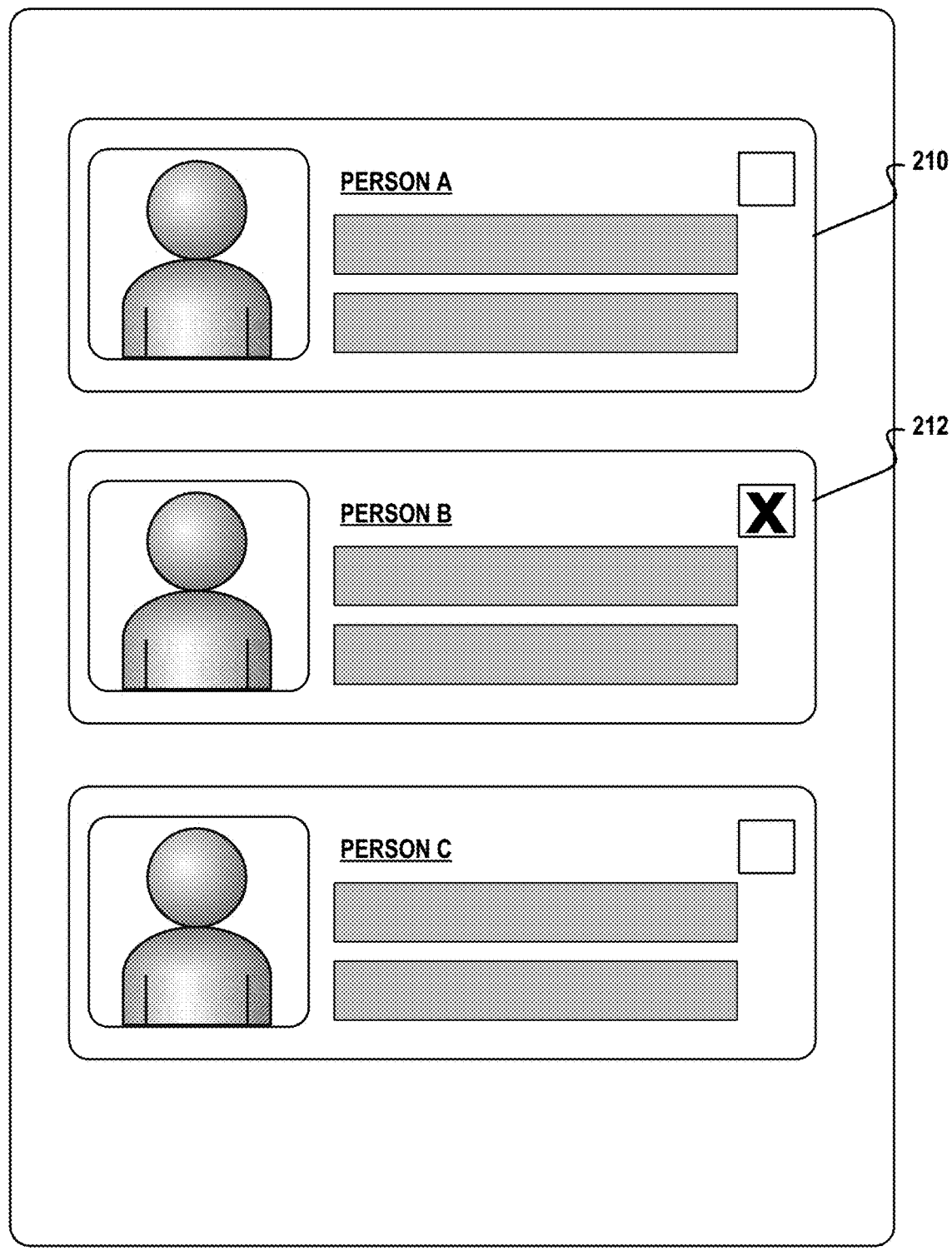
FIG. 2 illustrates an example event convergence application in accordance with respective examples.

FIG. 2 illustrates an example event convergence application 200 in accordance with respective examples. The application 200 may run on a staff device and receives beacons from nearby patients. The application may retrieve patient information for each nearby patient, e.g., 210 and 212. The information may include the patient's name, a patient image, and relevant information. This information may be displayed within the application 200. A staff member may select one or more patients 212. The staff member may provide additional observational information for each selected patient 212. When the information is confirmed, the application submits an observation log for each selected patient 212.

Figure 3:
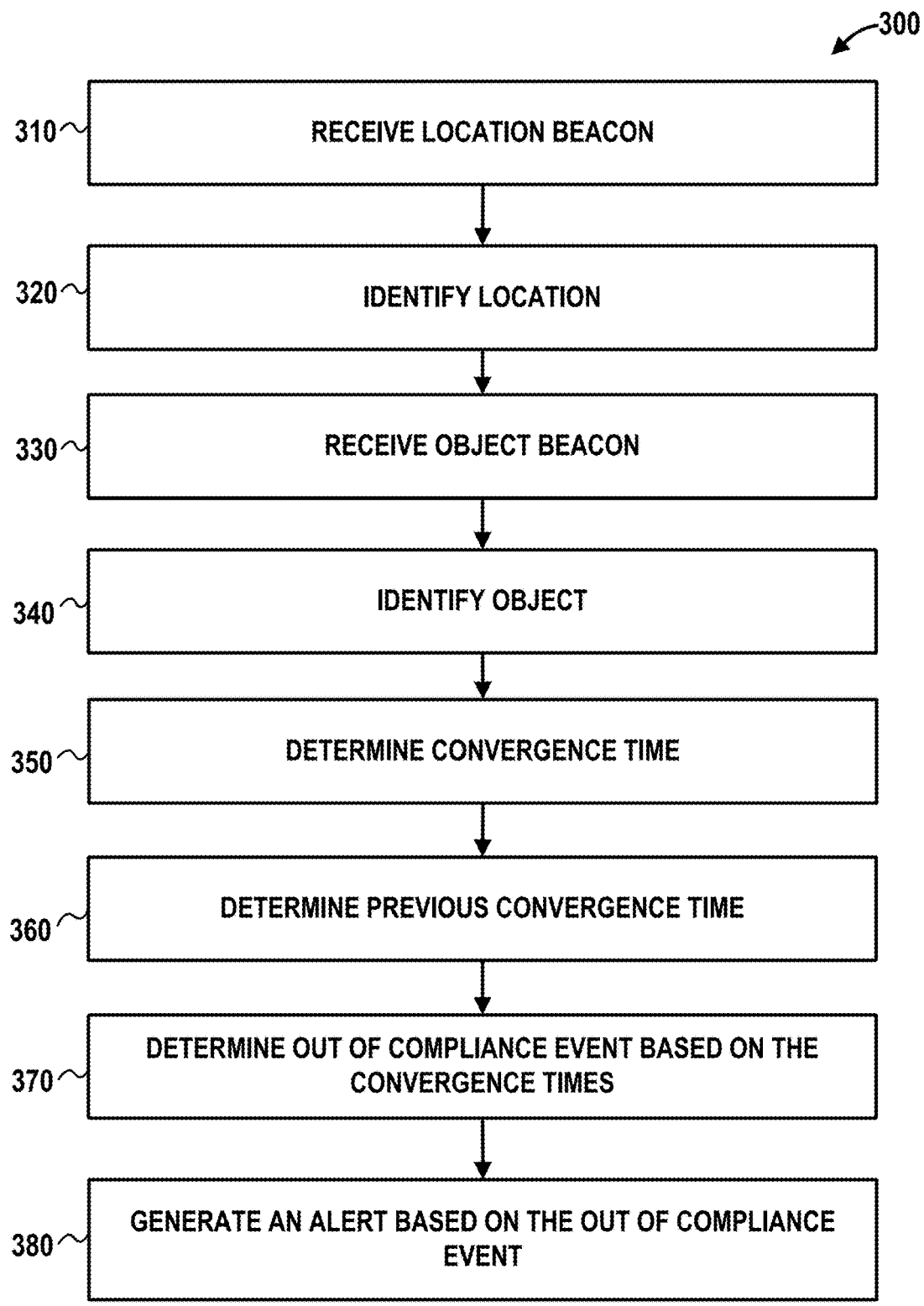
FIG. 3 is a diagram illustrating a flow diagram of a process for systemic certainty of event convergence in accordance with respective examples.

FIG. 3 is a diagram illustrating a flow diagram of a process 300 for systemic certainty of event convergence in accordance with respective examples. At 310, a device receives a first beacon that is transmitted from a beacon transmitter. The beacon transmitter is installed at a fixed location and does not typically move locations. Accordingly, the first beacon may be thought of as a location beacon. The location beacon includes information that identifies the first location. At 320, the location is identified from the beacon information. In an example, a remote server determines the location. In other examples, the device that receives the first beacon identifies the location. At 330, a second beacon is received at the device. The second beacon is transmitted from a beacon transmitter. In an example, the second beacon is transmitted from a wearable device worn by a patient of a medical facility. At 340, the object, such as a patient, associated with the second beacon is determined. When the beacon corresponds with a patient, the beacon can be considered a patient beacon. Similar with determining the location, either the device that receives the second beacon or a remote server may determine the object from information contained within the second beacon.

At 350, a current convergence time of the device and the object is determined based on the receiving the first and second beacon. In an example, the convergence time may be the later of the timestamps associated with the receipt of the beacons. In another example, the convergence time is either the receipt time of the first beacon or the receipt time of the second beacon. At 360, a previous convergence time associated with the object is determined. The previous convergence time may be the last time when the object was within the vicinity of a staff device or was observed.

At 370, an out of compliance event based on the current convergence time and the previous convergence time is determined. For example, an out of compliance event may be determined when the amount of time between the current convergence time and the last observation of a patient is longer than a predetermined threshold. At 380, an alert is generated based on the out of compliance event. The alert may be sent to staff members associated with the object or patient. The alert may be a message displayed in an application, sent as a text message, sent over a PA system.

In addition to receiving one object beacon, the device may receive multiple beacons. The multiple beacons may include multiple patient beacons. From these patient beacons, a number of patients may be identified. An observation regarding each of the number of patients may be logged. For example, a list of nearby patients may be displayed on the device. FIG. 2 provides such an example. Images for the patients may be determined. In an example, a remote server determines the images. In another example, the device includes patient images. These images are retrieved by the device and displayed on the device.

In an example, the device receives login credentials from the user of the device. For example, the user may be a staff member. The login credentials may be a username and password, bio security data, etc. The login credentials are verified. Once verified, the staff member's identification may be included in observation data. In another example, the staff member is also wearing a beacon transmitter that transmits information that identifies the staff member. The device may receive this information. The device may identify the staff member from the information from the staff member's beacon transmitter. In another example, the login credentials combined with the staff member's beacon information may be combined to verify the user of the device. Observation information may include the staff member's beacon information and indication that the staff member is successfully logged in.

In another example, a staff member is provided with a list of locations that are to be visited by the staff member. In addition, the staff member may be provided with a list of patients that are supposed to be located in each of the list of locations. The list of patients may include an image of each of the patients. The staff may use the images to quickly identify the patients.

In some examples, observing a patient may include collecting patient data. In an example, the patient data may include taking a picture of the patient. Facial recognition may be employed to analyze the image to identify the patient within the image. This image analysis may act as a confirmation that the patient was actually visited by a staff member using the device that provided an observation log. In another example, the device may collect a video of the patient. The video of the patient may be analyzed to determine the patient is breathing. This breathing indication may be included in the observation data sent from the device. In an example, the video is captured using an infrared camera that allows breathing determination analysis to be done during the evening. In another example, a thermal camera is used to detect the movement of warm breath from the patient.

In another example, video recorded from a camera, such as a camera that is part of a CCTV system, is accessed. For example, the convergence time along with the location of a convergence may be used to query a camera that records an area within the location. The location may be used to identify the appropriate camera or cameras. The convergence time may be used to determine which portion of recorded video from the cameras is relevant to the convergence. A portion of the video covering a portion or all of the convergence may be retrieved. The portion of the video may be stored as further proof of the convergence. In addition, the staff member, the patient, or both of the convergence may be identified in the portion of the video.

In another example, a remote server or a device may determine that a patient has not been observed for more than a predetermined amount of time, e.g., 5 minutes, 10 minutes, 15 minutes, etc. Based on this determination, one or more staff members assigned to the patient may be identified. An alert that indicates the patient, the patient's last known location, and time of last observation may be sent to the assigned staff members. Staff members may then go an observe the patient based on receiving the alert. Such an alert helps achieve compliance or minimize out of compliance with a safety protocol.

The amount of time a staff member or a patient stays within an area may also be determined and logged. For example, when a staff members visits a room a timer can be started. Once the staff member leaves the room, the timer may be stopped and included as a total time observed data point in an observation log. The amount of time may be used in determining a facility being in or out of compliance. A device may determine a staff member has entered a room when the strongest received location beacon is different from the previous strongest received location beacon. To ensure that rapid change of location does not occur, the strongest received location beacon may have to be received multiple times to be considered a change in location. In another example, certain beacons are indicated as a location where the amount of time spent near the location beacon is to be recorded. For example, a hand washing station may include an associated beacon transmitter. The device may receive the beacon and determine the beacon is from a hand washing station and that the amount of time spent at the hand washing station should be recorded. Accordingly, a timer is started. Once the staff member leaves the vicinity of the hand washing station, the timer is stopped and may be included in an observation report or separate data message sent to the remote server. In one example, the distance between the staff member and the hand washing station may be determined from the received signal strength indicator of the received beacon. From the RSSI the distance between the beacon transmitter and the device may be determined. Once this distance is greater than a predetermined threshold, the device is considered to have moved out of the vicinity of the beacon transmitter. In one example, the threshold is based on the beacon identifier.

In another example, the system may be used to determine a plausibility of an event. For example, if a person says they were assaulted by someone the system may be used to verify that the two individuals were near one another during the relevant period of time. If the logged data shows that the individuals were not near one another or that they were near one another for a brief period of time may indicate that the assault did not happen. Conversely, if the two individuals were close to one another the assault is more plausible. In addition, the logged data may be used to determine other individuals who may have witnessed the assault.

The described systems may be used in various different facilities other than health facilities. For example, schools, prisons, office buildings, etc., may all have location beacon transmitters installed. The location beacon transmitters combined with wearable transmitters worn be individuals or objects within those locations allow the benefits of the described systems to be realized.

The above examples illustrate a system of monitoring convergences between staff and patients. The convergences are measured, identified, and logged with minimal input from the staff and potentially no input from patients. As the disclosed examples do not rely on users entering data, but rather collecting data from the monitored environment, the fallibility of users is reduced if not wholly eliminated. Logs of the convergences may then be used to show a systemic certainty of compliance with a safety protocol. Any out of compliance events can also be identified. Using the out of compliance events, staff may receive additional training or additional resources may be provided. In addition with real time alerting of out of compliance events, the amount of time a facility is out of compliance with a safety protocol can be minimized. The disclosed system, therefore, helps ensure greater patient safety and well being and reduced costs of facilities for being out of compliance.

In another example, the event may be an event that needs to be verified. For example, the event may be an alleged assault or may be an allegation that someone was in a restricted area. As another example, the event may be an alleged theft. To verify an event, the individuals involved with the event are identified. For example, an event may occur on a cruise ship. The individuals may be identified via the ship's passenger list. In addition, an identifier may be determined for each individual associated with the event. The identifier may be associated with a beacon transmitter that is worn by an individual. Receipt of beacons from the beacon transmitter may be used to determine the location of an individual.

Once the individuals have been identified, a location service may be queried to determine the location of each individual over a period of time. The period of time may be the time period of time with the time of the event at the center of the time period. For example, if an event occurred at 5:15 pm, the time period may be 4:15 through 6:15 pm. The location of each individual during this time period may be determined. In addition, the convergence on the individuals during this time may be determined. The convergence is based on determining the beacon transmitters of individuals involved with the event where proximate to one another. In an example, proximate may be individuals that are within 5 feet, 10 feet, 25 feet, etc., of one another. In another example, proximate may mean that the individuals were within the same room.

Integration with video systems may also be done to provide relevant video. For example, the location of each individual during the time period may be used to determine which camera or cameras an individual should be seen on during the time period. The relevant video feed from the camera or cameras may be retrieved for each individual. In this example, a video feed that may be compiled from videos from different cameras may be generated for each individual. The video feed may then been reviewed to determine if an event occurred. In an example, an individual may take their beacon transmitter off before the event occurs. Even in this example, if one person is using a beacon transmitter, relevant location data and video data may be retrieved. In an example, facial recognition software may be used on the video feed to further identify individuals within the video feed.

Figure 4:
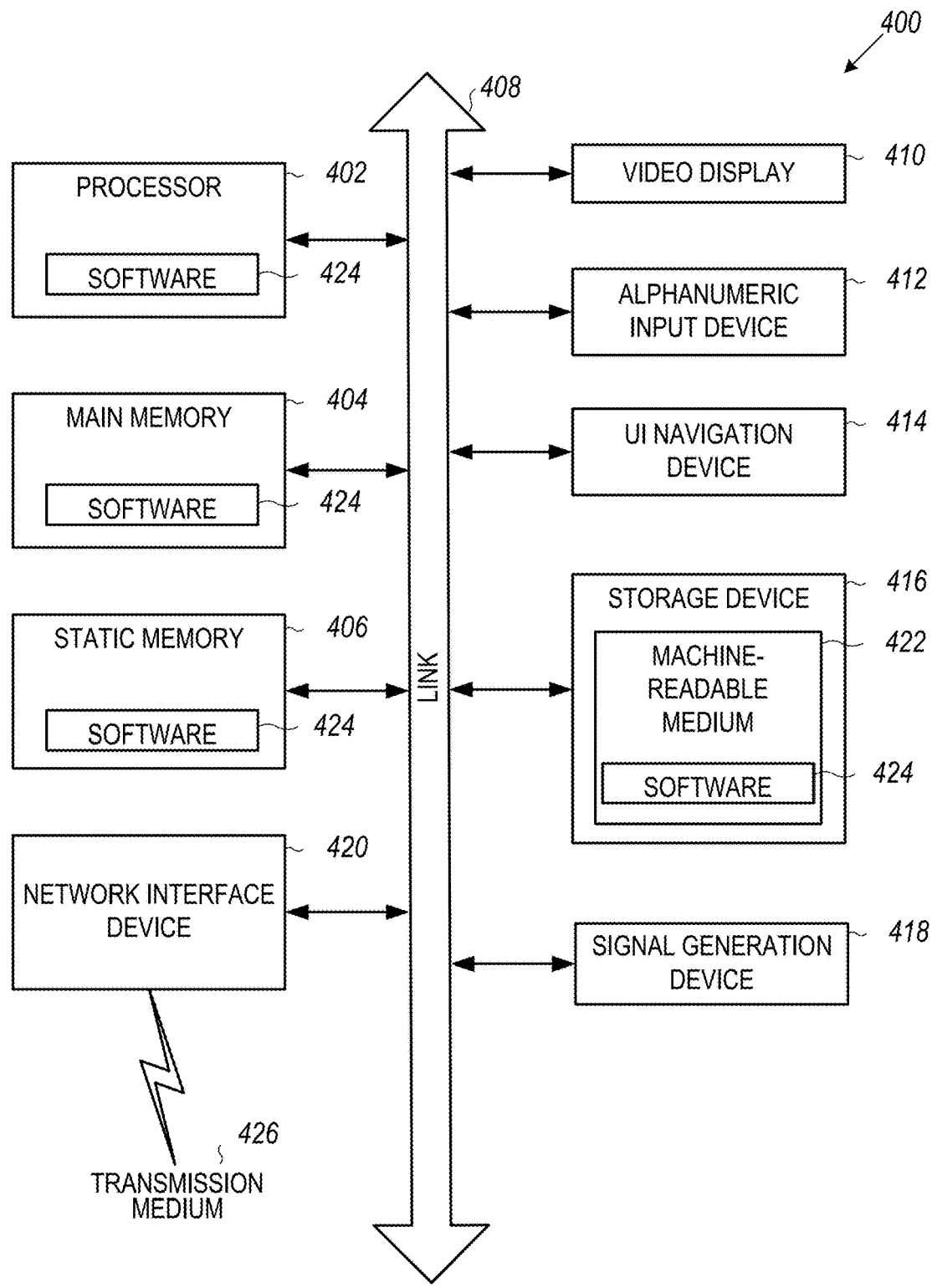
FIG. 4 is an example computing device that can be used in conjunction with the technologies described herein.

FIG. 4 is an example computing device that can be used in conjunction with the technologies described herein. In alternative embodiments, the computing device 400 may operate as a standalone device or may be connected (e.g., networked) to other computing devices. In a networked deployment, the computing device 400 may operate in the capacity of a server communication device, a client communication device, or both in server-client network environments. In an example, the computing device 400 may act as a peer computing device in peer-to-peer (P2P) (or other distributed) network environment. The computing device 400 may be a beacon reader, personal computer (PC), a tablet PC, a set top box (STB), a personal digital assistant (PDA), a mobile telephone, a smart phone, a web appliance, a network router, switch or bridge, or any computing device capable of executing instructions (sequential or otherwise) that specify actions to be taken by that computing device. Further, while only a single computing device is illustrated, the term "computing device" shall also be taken to include any collection of computing devices that individually or jointly execute a set (or multiple sets) of instructions to perform any one or more of the methodologies discussed herein, such as cloud computing, software as a service (SaaS), other computer cluster configurations. Computing device may be an implementation of a claimed device, a device that runs the application associated with the UI illustrated in FIG. 2, and may perform the method of FIG. 3.

Computing device 400 may include a hardware processor 402 (e.g., a central processing unit (CPU), a graphics processing unit (GPU), a hardware processor core, or any combination thereof), a main memory 404 and a static memory 406, some or all of which may communicate with each other via a link (e.g., bus) 408. The computing device 400 may further include a display unit 400, an input device 412 (e.g., a keyboard), and a user interface (UI) navigation device 414 (e.g., a mouse). In an example, the display unit 410, input device 412, and UI navigation device 414 may be a touch screen display. In an example, the input device 412 may include a touchscreen, a microphone, a camera (e.g., a panoramic or high-resolution camera), physical keyboard, trackball, or other input devices.

The computing device 400 may additionally include a storage device (e.g., drive unit) 416, a signal generation device 418 (e.g., a speaker, a projection device, or any other type of information output device), a network interface device 420, and one or more sensors, such as a global positioning system (GPS) sensor, compass, accelerometer, motion detector, or other sensor. The computing device 400 may include an input/output controller 428, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.) via one or more input/output ports.

The storage device 416 may include a computing-readable (or machine-readable) storage media 422, on which is stored one or more sets of data structures or instructions 424 (e.g., software) embodying or utilized by any one or more of the techniques or functions described herein. In an example, at least a portion of the software may include an operating system and/or one or more applications (or apps) implementing one or more of the functionalities described herein. The instructions 424 may also reside, completely or at least partially, within the main memory 404, within the static memory 406, and/or within the hardware processor 402 during execution thereof by the computing device 400. In an example, one or any combination of the hardware processor 402, the main memory 404, the static memory 406, or the storage device 416 may constitute computing device (or machine) readable media.

While the computer-readable storage media 422 is illustrated as a single medium, a "computer-readable storage media" or "machine-readable storage media" may include a single medium or multiple media (e.g., a centralized or distributed database, and/or associated caches and servers) configured to store the one or more instructions 424.

In an example, a computer-readable storage media or machine-readable storage media may include any medium that is capable of storing, encoding, or carrying instructions for execution by the computing device 400 and that cause the computing device 400 to perform any one or more of the techniques of the present disclosure, or that is capable of storing, encoding or carrying data structures used by or associated with such instructions. Non-limiting computer-readable storage media examples may include solid-state memories, and optical and magnetic media. Specific examples of computer-readable storage media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; Random Access Memory (RAM); and optical media disks. The computer-readable storage media is non-transitory in that the storage media does not consist of transitory propagating signals.

The instructions 424 may further be transmitted or received over a communications network 426 using a transmission medium via the network interface device 420 utilizing any one of a number of transfer protocols (e.g., frame relay, interne protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, a Long Term Evolution (LTE) family of standards, a Universal Mobile Telecommunications System (UMTS) family of standards, peer-to-peer (P2P) networks, among others. The network interface device 420 may use the transfer protocols to transmit data using transitory propagating signals.

In an example, the network interface device 420 may include one or more physical jacks (e.g., Ethernet, coaxial, or phone jacks) or one or more antennas to connect to the communications network 426. In an example, the network interface device 420 may include one or more wireless modems, such as a Bluetooth modem, a Wi-Fi modem or one or more modems or transceivers operating under any of the communication standards mentioned herein. In an example, the network interface device 420 may include a plurality of antennas to wirelessly communicate using at least one of single-input multiple-output (SIMO), multiple-input multiple-output (MIMO), or multiple-input single-output (MISO) techniques. In some examples, the network interface device 420 may wirelessly communicate using Multiple User MIMO techniques. In an example, a transmission medium may include any intangible medium that is capable of storing, encoding or carrying instructions for execution by the computing device 400, and includes digital or analog communications signals or like communication media to facilitate communication of such software.

Any of the computer-executable instructions for implementing the disclosed techniques as well as any data created and used during implementation of the disclosed embodiments can be stored on one or more computer-readable storage media. The computer-executable instructions can be part of, for example, a dedicated software application or a software application that is accessed or downloaded via a web browser or other software application (such as a remote computing application). Such software can be executed, for example, on a single local computer (e.g., any suitable commercially available computer) or in a network environment (e.g., via the Internet, a wide-area network, a local-area network, a client-server network (such as a cloud computing network), or other such network) using one or more network computers.

The above description is intended to be illustrative, and not restrictive. For example, the above-described examples (or one or more aspects thereof) may be used in combination with others. Other embodiments may be used, such as by one of ordinary skill in the art upon reviewing the above description. Further, the following claims are hereby incorporated into the Detailed Description, with a claim standing on its own as a separate embodiment. The scope of the embodiments disclosed herein is to be determined with reference to the appended claims, along with the full scope of equivalents to which such claims are entitled.

What is claimed is:

1. A method for identifying a convergence of objects, the method comprising operations performed using an electronic processor, the operations comprising:
   receiving, at a device, a first beacon from a beacon transmitter located within a first location;
   identifying, based on the first beacon, the first location;
   receiving, at the device, a second beacon transmitted from a wearable worn by a patient;
   identifying, based on the second beacon, the patient associated with the second beacon;
   determining a current convergence time of the device and the patient based on the receiving the first beacon or the receiving the second beacon;
   determining a previous convergence time of the device and the wearable based on a previous second beacon received from the wearable;
   determining a duration of time between the current convergence time and the previous convergence time;
   determining the duration of time is greater than a predetermined threshold;
   determining an out of compliance event based on the duration of time being greater than the predetermined threshold;
   generating an alert based on the out of compliance event, wherein the alert comprises the first location;
   sending the current convergence time, and indication of the first location, and an indication of the patient to a remote server;
   determining a camera, from a plurality of cameras, that records video data of the first location;
   determining a time period of relevant video based on the current convergence time;
   retrieving from the video data of the first location from the camera a portion of the video data based on the determined time period of relevant video data; and
   identifying, using facial recognition, a user of the device within the retrieved video data.

2. The method of claim 1, further comprising:
   receiving, at the device, a plurality of beacons, wherein the plurality of beacons comprises the second beacon;
   identifying a plurality of patients based on the plurality of beacons; and
   logging an observation of each of the plurality of patients.

3. The method of claim 2, further comprising:
   retrieving an image of each of the plurality of patients; and
   displaying, on the device, the image of each of the plurality of patients.

4. The method of claim 1, further comprising:
   receiving, at the device, login credentials associated with an individual; and
   verifying the login credentials.

5. The method of claim 4, further comprising:
   determining a plurality of locations to be visited by the individual, wherein the plurality of locations comprises the first location; and
   determining the patient associated with the second beacon is supposed to be located within the first location.

6. The method of claim 1, further comprising:
   capturing, from the device, an image of the patient;
   recognizing the patient from the image of the patient; and
   confirming the patient was visited by device based in part of the recognizing the patient from the image of the patient.

7. The method of claim 1, further comprising:
   capturing, from the device, a video of the patient;
   recognizing a breathing indication of the patient from the video;
   providing the breathing indication of the patient along with the current convergence time to a remote device.

8. The method of claim 7, wherein the device captures the video of the patient using an infrared camera.

9. The method of claim 1, further comprising:
   determining the patient has not been observed for more than a predetermined amount of time;
   determining the user responsible for observing the patient; and
   send an alert to the device associated with the user to observe the patient.

10. The method of claim 9, wherein the alert comprises an indication of the first location.

11. The method of claim 10, further comprising sending the alert to a second user responsible for observing the patient.

12. The method of claim 1, further comprising:
    receiving, at the device, a third beacon;
    starting, based on the receiving of the third beacon, a timer;
    monitoring continued receipt of the third beacon over a period of time;
    determining, at the device, a distance between the device and a transmitter of the third beacon;
    stopping the timer based on the distance being greater than a predetermined threshold; and
    sending an indication of the third beacon and a value of the timer to a remote device.

13. The method of claim 1, further comprising:
    receiving, at the device, a third beacon transmitted from a wearable worn by a staff member; and
    identifying, based on the third beacon, the staff member associated with the third beacon.

14. A system to identify a convergence of objects, the system comprising:
    a location beacon transmitter fixed at a first location and configured to transmit a location beacon within the first location, wherein the location beacon identifies the first location;
    a patient beacon transmitter configured to attached to a moveable object and to transmit a patient beacon, wherein the patient beacon identifies the moveable object;
    a plurality of cameras, wherein camera is configured to record video data, and wherein a first camera records video data of the first location;
    an electronic processor of a device configured to:
      receive the location beacon from the location beacon transmitter;
      receive the patient beacon transmitted from the patient beacon transmitter; and
      transmit the location beacon and the patient beacon to a remote server;
    the remote server configured to:
      identify, based on the location beacon, the first location;

identify, based on the patient beacon, the moveable object;

determine a current convergence time of the device and the moveable object based on the receiving the location beacon or the receiving the patient beacon;

determine a previous convergence time of the device and the moveable object based on a previous patient beacon received from the patient beacon transmitter;

determine a duration of time between the current convergence time and the previous convergence time;

determine the duration of time is greater than a predetermined threshold;

determine an out of compliance event based on the duration of time being greater than the predetermined threshold;

generate an alert based on the out of compliance event, wherein the alert comprises the first location; and determine the first camera, from the plurality of cameras, based on identified first location;

determine a time period of relevant video data based on the current convergence time;

retrieve from the video data of the first location from the first camera a portion of the video data based on the determined time period of relevant data; and identify, using facial recognition, a user of the device within the retrieved video data.

15. The system of claim 14, wherein the electronic processor is further configured to:
receive a third beacon transmitted from a wearable worn by a staff member; and
identifying, based on the third beacon, the staff member associated with the third beacon.

16. The system of claim 14, wherein the electronic processor is further configured to:
receive a plurality of beacons, wherein the plurality of beacons comprises the second beacon; and
logging an observation of each of the plurality of patients.

17. A non-transitory computer-readable storage medium storing computer-executable instructions that when executed by a processor cause the processor to perform operations comprising:
receiving, at a device, a first beacon from a beacon transmitter located within a first location;
identifying, based on the first beacon, the first location;
receiving, at the device, a second beacon transmitted from a wearable worn by a patient;
identifying, based on the second beacon, the patient associated with the second beacon;
determining a current convergence time of the device and the patient based on the receiving the first beacon or the receiving the second beacon;
determining a previous convergence time of the device and the wearable based on a previous second beacon received from the wearable;
determining a duration of time between the current convergence time and the previous convergence time;

determining the duration of time is greater than a predetermined threshold;

determining an out of compliance event based on the duration of time being greater than the predetermined threshold;

generating an alert based on the out of compliance event, wherein the alert comprises the first location;

sending the current convergence time, an indication of the first location, and an indication of the patient to a remote server;

determining a camera, from a plurality of cameras, that records video data of the first location;

determining a time period of relevant video data based on the current convergence time;

retrieving from the video data of the first location from the camera a portion of the video data based on the determined time period of relevant video data; and identifying, using facial recognition, a user of the device within the retrieved video data.

18. The non-transitory computer-readable storage medium of claim 17, wherein the operations further comprise:
receiving, at the device, a plurality of beacons, wherein the plurality of beacons comprises the second beacon; and
logging an observation of each of the plurality of patients.

19. The method of claim 1, further comprising:
receiving, at the device, a third beacon from the beacon transmitter located within the first location;
receiving, at the device, a fourth beacon transmitted from the wearable worn by the patient;
determining a second convergence time of the device and the patient based on the receiving the third beacon or the receiving the fourth beacon, wherein the second convergence time is later than the current convergence time; and
determining a total out of compliance time as a duration between when the predetermined threshold was reached from the previous convergence time and the second convergence time.

20. The non-transitory computer-readable storage medium of claim 17, wherein the operations further comprise:
receiving, at the device, a third beacon from the beacon transmitter located within the first location;
receiving, at the device, a fourth beacon transmitted from the wearable worn by the patient;
determining a second convergence time of the device and the patient based on the receiving the third beacon or the receiving the fourth beacon, wherein the second convergence time is later than the current convergence time; and
determining a total out of compliance time as a duration between when the predetermined threshold was reached from the previous convergence time and the second convergence time.

* * * * *